United States Patent [19]

Gotoh

[11] Patent Number: 4,970,031

[45] Date of Patent: Nov. 13, 1990

[54] PROCESS FOR PREPARING MICROCAPSULES WITH CONTROLLED-RELEASE

[75] Inventor: Masao Gotoh, Sagamihara, Japan

[73] Assignee: NOK Corporation, Tokyo, Japan

[21] Appl. No.: 201,189

[22] Filed: Jun. 2, 1988

[51] Int. Cl.$^5$ .......................... B01J 13/20; B01J 13/16

[52] U.S. Cl. ...................................... 264/4.3; 264/4.7; 424/455; 424/497; 424/501; 514/963

[58] Field of Search .................... 264/4.3, 4.7, 4.33

[56]  References Cited

U.S. PATENT DOCUMENTS

| | | | |
|---|---|---|---|
| 3,565,559 | 2/1971 | Sato et al. | 264/4.3 X |
| 3,900,669 | 8/1975 | Kiritani | 264/4.7 X |
| 4,193,889 | 3/1980 | Baatz et al. | 264/4.3 X |
| 4,407,957 | 10/1983 | Lim | 264/4.3 |
| 4,428,983 | 1/1984 | Nehen et al. | 264/4.7 X |
| 4,464,434 | 8/1984 | Davis | 264/4.3 X |
| 4,490,313 | 12/1984 | Brown et al. | 264/4.7 |
| 4,683,092 | 7/1987 | Tsang | 264/4.3 |

Primary Examiner—Richard D. Lovering
Assistant Examiner—John M. Covert
Attorney, Agent, or Firm—Fred Philpitt

[57] ABSTRACT

Microcapsules with controlled-release are prepared by subjecting microcapsules encasing an aqueous solution of a substance to be released from the microcapsules under control to a heat treatment in an aqueous solution containing the substance same with the substance to be released from the microcapsules, while selecting a heating temperature.

4 Claims, No Drawings

PROCESS FOR PREPARING MICROCAPSULES WITH CONTROLLED-RELEASE

BACKGROUND OF THE INVENTION

1. Field of the Invention

This invention relates to a process for preparing microcapsules with controlled-release, and more particularly to a process for producing microcapsules with controlled-release whose releasability can be controlled.

2. Description of the Prior Art

Heretofore, microcapsules have been prepared by interfacial polymerization, in-situ polymerization, submerged curing-coating, coacervation, spray drying, inorganic walling, or the like.

The protectivity of the microcapsule skin film and the releasability of a substance enclosed by the skin film can be dynamically utilized and thus the microcapsules have been widely utilized also in effective utilization of the releasability of the substance enclosed by the skin film as a substance to be released from microcapsules under control, such as continued maintenance and/or control of demonstration of medical or chemical effects of medicaments or agricultural chemicals, continued maintenance of perfume, flavor, etc., and control of the reactivity of immobilized enzymes, prepolymers, etc.

In these applications, it is practically very important to control the releasability of capsules, and the releasability has been tried to be controlled by adjusting the thickness or permeability of the skin film. However, it has been difficult to control the releasability by such adjustments.

SUMMARY OF THE INVENTION

An object of the present invention is to provide microcapsules with controlled-release, where the releasability of microcapsules can be controlled as desired.

Another object of the present invention is to provide a process for preparing such microcapsules with controlled-release.

DETAILED DESCRIPTION OF THE INVENTION

These objects of the present invention can be attained by subjecting microcapsules encasing an aqueous solution of a substance to be released from the microcapsules under control to a heat treatment in an aqueous solution containing the substance same with the substance to be released, thereby preparing microcapsules with controlled-release.

Microcapsules encasing an aqueous solution of a substance to be released from the microcapsules under control can be prepared according to the afore-mentioned various microcapsulation procedures, preferably by interfacial polymerization.

The interfacial polymerization is carried out through an interfacial reaction of an aqueous solution containing about 0.1 to about 1% by weight of a hydrophilic monomer with a solution containing about 0.1 to about 10% by weight of a hydrophobic monomer in a water-immiscible, inert organic solvent, such as n-hexane, etc.

Microcapsulation based on the interfacial polymerization is carried out by dropwise adding an aqueous hydrophilic monomer solution to an organic solvent solution of a hydrophobic monomer through a trickling jig such as a microsyringe, etc. at a trickling rate of about 0.001 to about 0.2 ml per drop at a temperature of about 10 to about 30° C., preferably with stirring at a stirring speed of 10 revolutions per second or less.

Typical combinations of the hydrophilic monomer with the hydrophobic monomer for the microcapsulation are given below:

| Hydrophilic monomer | Hydrophobic monomer | Skin film formed |
|---|---|---|
| Polyalkyleneimine | Diisocyanate | Polyurethane |
| Diamine | Dicarboxylic acid dihalide | Polyamide |
| Glycol | Dicarboxylic acid dihalide | Polyester |

The substance to be released from microcapsules under control is added to aqueous hydrophilic monomer solution at the microcapsulation to make a concentration of about 0.1 to about 1% by weigth, and thus is encased as an aqueous solution in the formed microcapsules.

The substance to be released from the microcapsules under control includes agricultural chemicals such as methylparathion, etc., medicaments such as α-heparin, aspirin, acetaminophen, papaverine, tetracycline, etc., perfumes such as aromatic esters, higher alcohols, synthetic perfumes, etc., flavors such as butyric acid, etc., immobilized enzyme, prepolymers, etc.

The thus formed microcapsules are heat treated in an aqueous solution containing the substance same with the substance to be released from the microcapsules in order to control the release rate of the substance encased in the microcapsules. The same aqueous solution at the same concentration as encased in the microcapsules is used as the aqueous solution for the heat treatment, and the heat treatment is carried out at a temperature of about 30° to about 90° C. for about 5 to about 20 minutes. The reason why the same aqueous solution at the same concentration is used for the heat treatment is to prevent diffusion of the substance encased in the microcapsules into the aqueous solution used for the heat treatment. As a result of the heat treatment, the thickness of microcapsules is increased and pore sizes are decreased. That is, the controlled-release rate is lowered.

According to the present process, microcapsules with controlled-release can be obtained by subjecting microcapsules encasing a substance to be released therefrom under control, formed by interfacial polymerization, etc., to a heat treatment in an aqueous solution containing the substances same with the substance to be released from the microcapsules, while selecting the heating temperature.

PREFERRED EMBODIMENTS OF THE INVENTION

The present invention will be described in detail below, referring to Examples.

EXAMPLE 1

0.8% by weight of polyethyleneimine and 0.05% by weight of polyethyleneglycol (molecular weight: 200) were dissolved in water purified by reverse osmosis to prepare an aqueous polyethyleneimine solution.

Separately, 100 ml of 0.5% by weight n-hexane solution of toluene diisocyanate was placed in a beaker and kept at a temperature of 25° C. and in a stirred state with a stirrer at a stirring speed of 2 revolutions per second.

The aqueous polyethyleneimine solution was taken into a microsyringe with a horizontal cut tip end by suction and dropwise added to the solution of toluene diisocyanate perpendicularly to the liquid surface at a rate of 0.01 ml per second, whereby microcapsules, about 2 mm in diameter, were formed.

Five polyethyleneglycol-encasing microcapsules thus formed were immersed in 5 ml of water and the polyethyleneglycol releasability was determined with a total organic carbon meter (TOC-10B, made by Shimazu Seisakusho K.K., Japan) while stirring the water with a stirrer at a stirring rate of 2 revolutions per second. It was found that the release rate was 2.65 $\mu g/min \cdot ml \cdot cm^2$. The skin film thickness of the microcapsules was determined to be about 25 $\mu m$ with an electron microscope.

Furthermore, the polyethyleneglycol-encasing microcapsules were immersed in an aqueous 0.05% by weight polyethyleneglycol solution in a beaker and heated at 50° C. or 70° C. for 10 minutes. The polyethyleneglycol releasability of the heat-treated microcapsules and the skin film thickness were determined in the same manner as above. The results are shown in the following Table 1.

TABLE 1

| Heating temperature (°C.) | Release rate ($\mu g/min \cdot ml \cdot cm^2$) | Skin film thickness ($\mu m$) |
| --- | --- | --- |
| 50 | 1.25 | about 28 |
| 70 | 0.90 | about 31 |

EXAMPLE 2

Microcapsules were prepared in the same manner as in Example 1, except that an aqueous 0.05% by weight solution of α-heparin (molecular weight: 17,000) was used at the formation and the heat treatment of microcapsules in place of the aqueous polyethyleneglycol solution.

The release rate and the skin film thickness of the thus prepared microcapsules were determined in the same manner as in Example 1 and are given in the following Table 2.

TABLE 2

| Heating temperature (°C.) | Release rate ($\mu g/min \cdot ml \cdot cm^2$) | Skin film thickness ($\mu m$) |
| --- | --- | --- |
| none | 0.50 | 26 |
| 50 | 0.30 | 30 |
| 70 | 0.15 | 32 |

EXAMPLE 3

0.4 moles of 1,6-hexamethylenediamine was dissolved in water purified by reverse osmosis to prepare 5 ml of the aqueous solution. The aqueous solution was placed in a beaker and kept at 4° C. over an ice bath. Butyric acid was added to the aqueous solution to make a concentration of 0.5% by weight, and the mixture was stirred at a stirring rate of 2 revolutions per second to prepare a 1,6-hexamethylenediamine solution.

Separately, 0.4 moles of sebacoyl dichloride was added to 50 ml of a mixture of cyclohexane and chloroform (4:1 by volume) and kept at 25° C. and in a stirred state with a etirrer at a stirring rate of 2 revolutions per second. Then, the 1,6-hexamethylenediamine solution was taken into a microsyringe by suction and dropwise added to the stirred solution at a trickling rate of 0.01 ml/min. to make microcapsules, about 1.0 mm in diameter and about 15 $\mu m$ in skin thickness (by electron microscope).

Five butyric acid-encasing microcapsules thus formed were immersed in 5 ml of water and the butyric acid releasability was determined with the same total organic carbon meter as used in Example 1, while stirring water with a stirrer at a stirrer rate of 2 revolutions per second. It was found that the release rate was 30 $\mu g/min \cdot ml \cdot cm^2$.

Furthermore, the butyric acid-encasing microcapsules were immersed in an aqueous 0.5% by weight butyric acid solution in a beaker and heated at 50° C. or 70° C. for 10 minutes, and the release rate and the skin film thickness of microcapsules were determined. The results are given in the following Table 3.

TABLE 3

| Heating temperature (°C.) | Release rate ($\mu g/min \cdot ml \cdot cm^2$) | Skin film thickness ($\mu m$) |
| --- | --- | --- |
| 50 | 18 | 18 |
| 70 | 10 | 20 |

What is claimed is:

1. A process for preparing controlled-release microcapsules which encase an aqueous solution containing a substance to be released from the microcapsule, which process comprises:
    (a) providing an aqueous solution that contains a hydrophilic monomer and a substance that is to be released from said microcapsules,
    (b) providing an organic solvent solution containing a hydrophobic monomer,
    (c) adding said aqueous solution dropwise to said organic solvent solution so as to form by interfacial polymerization microcapsules encasing said aqueous solution, and
    (d) immersing the microcapsules prepared in accordance with step (c) in a liquid bath maintained at a temperature of about 50°–90° C., said liquid bath being composed of an aqueous solution that contains the same substance that is set forth in step (a) in the same concentration as set forth in step (a).

2. A process according to claim 1 wherein said microcapsules in step (d) are immersed in said liquid bath for 5–20 minutes.

3. A process according to claim 2 wherein said liquid bath is maintained at a temperature of 50°–70° C.

4. A process according to claim 1 wherein said liquid bath is maintained at a temperature of 50°–70° C.

* * * * *